(12) United States Patent
McDonald et al.

(10) Patent No.: US 9,808,613 B2
(45) Date of Patent: Nov. 7, 2017

(54) SYSTEMS AND METHODS FOR IMPROVING RF COMPATIBILITY OF ELECTRICAL STIMULATION LEADS

(71) Applicant: BOSTON SCIENTIFIC NEUROMODULATION CORPORATION, Valencia, CA (US)

(72) Inventors: Matthew Lee McDonald, Pasadena, CA (US); Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 948 days.

(21) Appl. No.: 13/962,282

(22) Filed: Aug. 8, 2013

(65) Prior Publication Data

US 2014/0058487 A1    Feb. 27, 2014

Related U.S. Application Data

(60) Provisional application No. 61/693,104, filed on Aug. 24, 2012.

(51) Int. Cl.
*A61N 1/00* (2006.01)
*A61N 1/05* (2006.01)

(52) U.S. Cl.
CPC .............. *A61N 1/05* (2013.01); *A61N 1/056* (2013.01); *A61N 1/057* (2013.01); *A61N 2001/0578* (2013.01); *F04C 2270/041* (2013.01); *Y10T 29/4922* (2015.01)

(58) Field of Classification Search
CPC ........... A61N 1/05; A61N 1/056; A61N 1/057
USPC ........................................................ 607/116
See application file for complete search history.

(56) References Cited

U.S. PATENT DOCUMENTS

| 5,282,844 | A | 2/1994 | Stokes et al. |
| 6,181,969 | B1 | 1/2001 | Gord |
| 6,213,995 | B1 | 4/2001 | Steen et al. |

(Continued)

FOREIGN PATENT DOCUMENTS

EP    1935449 A1    6/2008

OTHER PUBLICATIONS

International Search Report and Written Opinion for International Patent Application No. PCT/US2013/054154 dated Oct. 28, 2013.

*Primary Examiner* — Nicole F Johnson
(74) *Attorney, Agent, or Firm* — Lowe Graham Jones PLLC; Bruce E. Black

(57) ABSTRACT

An implantable lead for stimulating patient tissue includes a lead body. A jacket is disposed over at least a portion of a length of the lead body. The jacket has an outer surface and an opposing inner surface. At least a portion of the outer surface of the jacket forms at least a portion of an outer surface of the lead. At least a portion of the inner surface of the jacket is open to the lead body. The jacket defines apertures each extending completely through the jacket. Electrodes are disposed along a distal end of the lead body. Terminals are disposed along a proximal end of the lead body. Conductors electrically couple the electrodes to the terminals. Conductor insulation is disposed over each of the conductors. At least a portion of the conductor insulation is in fluid communication with the local environment external to the lead via the apertures.

14 Claims, 8 Drawing Sheets

(56) References Cited

U.S. PATENT DOCUMENTS

| | | | |
|---|---|---|---|
| 6,216,045 B1 * | 4/2001 | Black | A61N 1/05 600/373 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,704,604 B2 | 3/2004 | Soukup et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,650,193 B2 | 1/2010 | Aron et al. | |
| 7,672,734 B2 | 3/2010 | Anderson et al. | |
| 7,761,165 B1 | 7/2010 | He et al. | |
| 7,844,344 B2 | 11/2010 | Wahlstrand et al. | |
| 7,853,332 B2 | 12/2010 | Olsen et al. | |
| 7,877,150 B2 | 1/2011 | Hoegh et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,280,526 B2 | 10/2012 | Wahlatrand | |
| 8,364,278 B2 | 1/2013 | Pianca et al. | |
| 2007/0150036 A1 | 6/2007 | Anderson | |
| 2007/0250039 A1 | 10/2007 | Lobbins et al. | |
| 2008/0147155 A1 * | 6/2008 | Swoyer | A61N 1/0551 607/116 |
| 2010/0241207 A1 | 9/2010 | Bluger | |
| 2011/0071604 A1 | 3/2011 | Wahlstrand et al. | |

\* cited by examiner

SYSTEMS AND METHODS FOR IMPROVING RF COMPATIBILITY OF ELECTRICAL STIMULATION LEADS

CROSS-REFERENCE TO RELATED APPLICATIONS

This application claims the benefit under 35 U.S.C. §119 (e) of U.S. Provisional Patent Application Ser. No. 61/693,104 filed Aug. 24, 2012, which is incorporated herein by reference.

FIELD

The present invention is directed to the area of implantable electrical stimulation systems and methods of making and using the systems. The present invention is also directed to electrical stimulation leads having jackets that promote fluid ingress into the lead, as well as methods of making and using the jackets, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead for stimulating patient tissue includes a lead body having a distal end, a proximal end, and a longitudinal length. A jacket is disposed over at least a portion of the longitudinal length of the lead body. The jacket has an outer surface and an opposing inner surface. At least a portion of the outer surface of the jacket forms at least a portion of an outer surface of the lead. At least a portion of the inner surface of the jacket is open to the lead body. The jacket defines a plurality of apertures along the outer surface of the lead with each of the plurality of apertures extending completely through the jacket to the inner surface. A plurality of electrodes is disposed along the distal end of the lead body. A plurality of terminals is disposed along the proximal end of the lead body. A plurality of conductors electrically couples the plurality of electrodes to at least one of the terminals. Conductor insulation is disposed over each of the plurality of conductors. At least a portion of the conductor insulation is in fluid communication with the local environment external to the lead via the plurality of apertures.

In another embodiment, a method for forming an implantable lead includes providing a lead with a lead body having a distal end, a proximal end, and a longitudinal length, where a plurality of electrodes is disposed along the distal end of the lead body, where a plurality of terminals is disposed along the proximal end of the lead body, where a plurality of conductors electrically couple the plurality of electrodes to at least one of the terminals, and where conductor insulation is disposed over each of the plurality of conductors. A jacket is disposed over at least a portion of the longitudinal length of the lead body. The jacket has an outer surface and an opposing inner surface. At least a portion of the outer surface of the jacket forms at least a portion of an outer surface of the lead. At least a portion of the inner surface of the jacket is open to the lead body. The jacket defines a plurality of apertures defined along the outer surface of the lead with each of the plurality of apertures extending completely through the jacket to provide at least a portion of the conductor insulation in fluid communication with the local environment external to the lead via the plurality of apertures.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to electrical stimulation leads having jackets that promote fluid ingress into the lead, as well as methods of making and using the jackets, leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Figure 1:
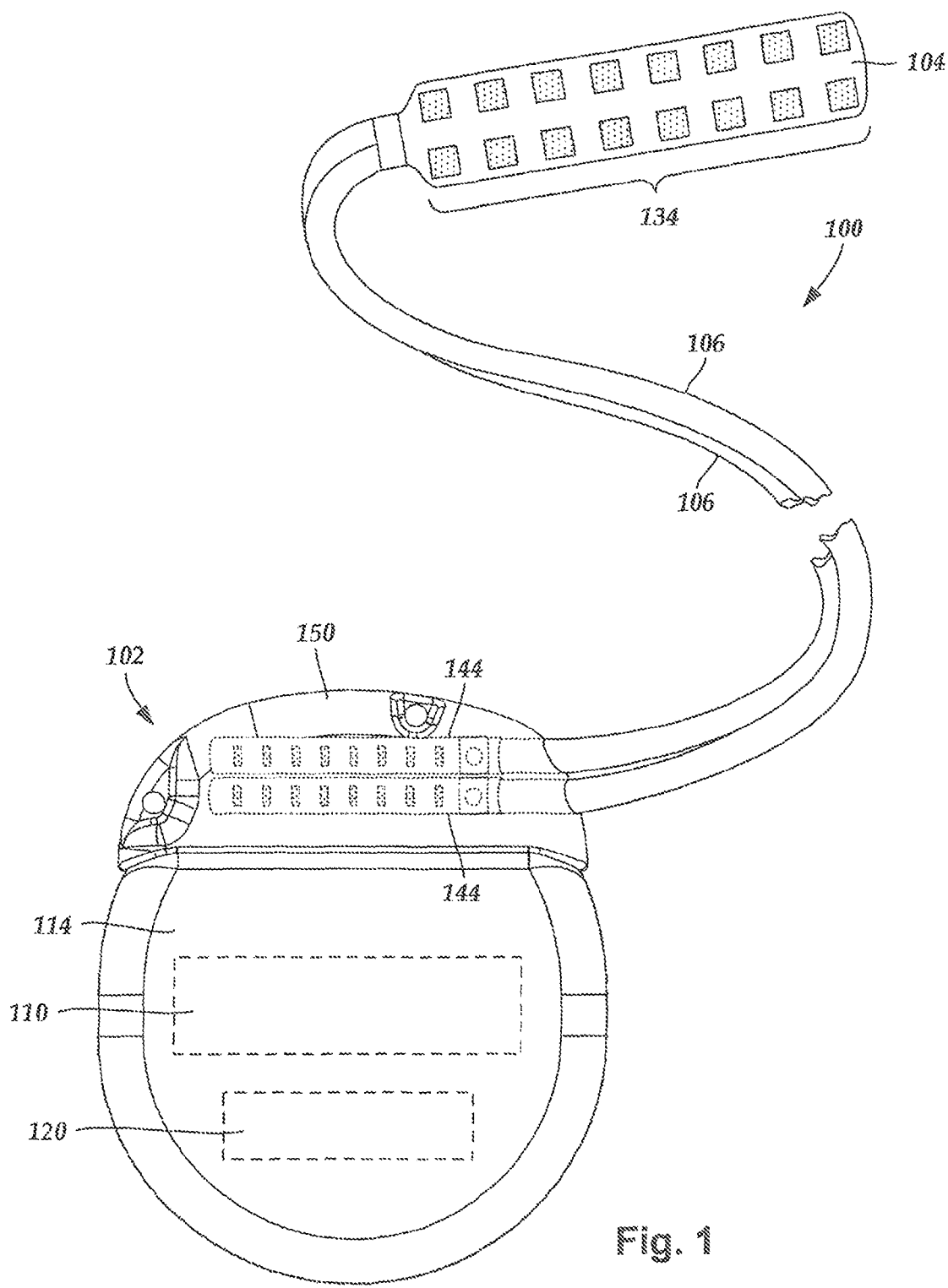
FIG. 1 is a schematic view of one embodiment of an electrical stimulation system that includes a paddle lead with a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
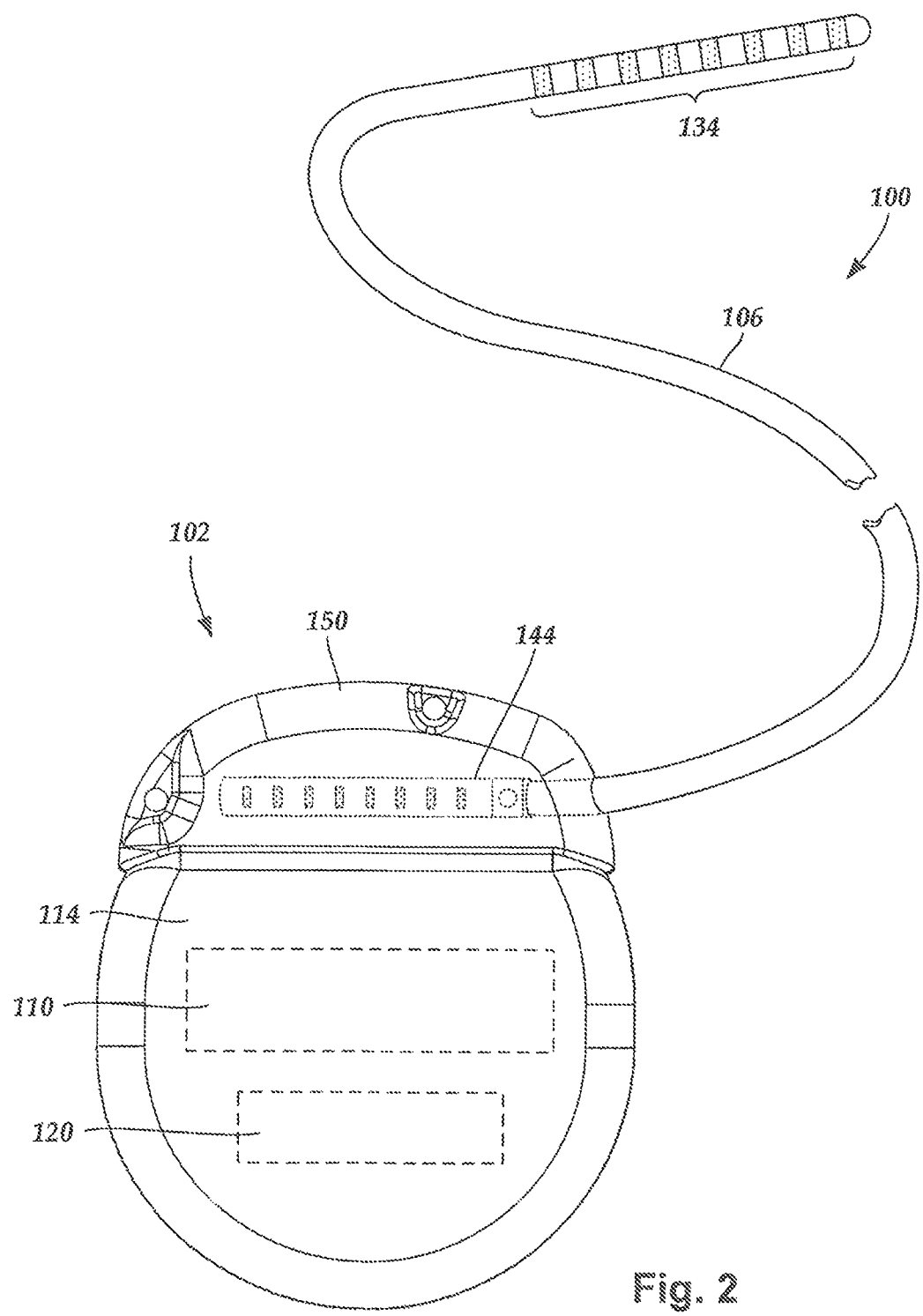
FIG. 2 is a schematic view of another embodiment of an electrical stimulation system that includes a percutaneous lead coupled to the control module of FIG. 1, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
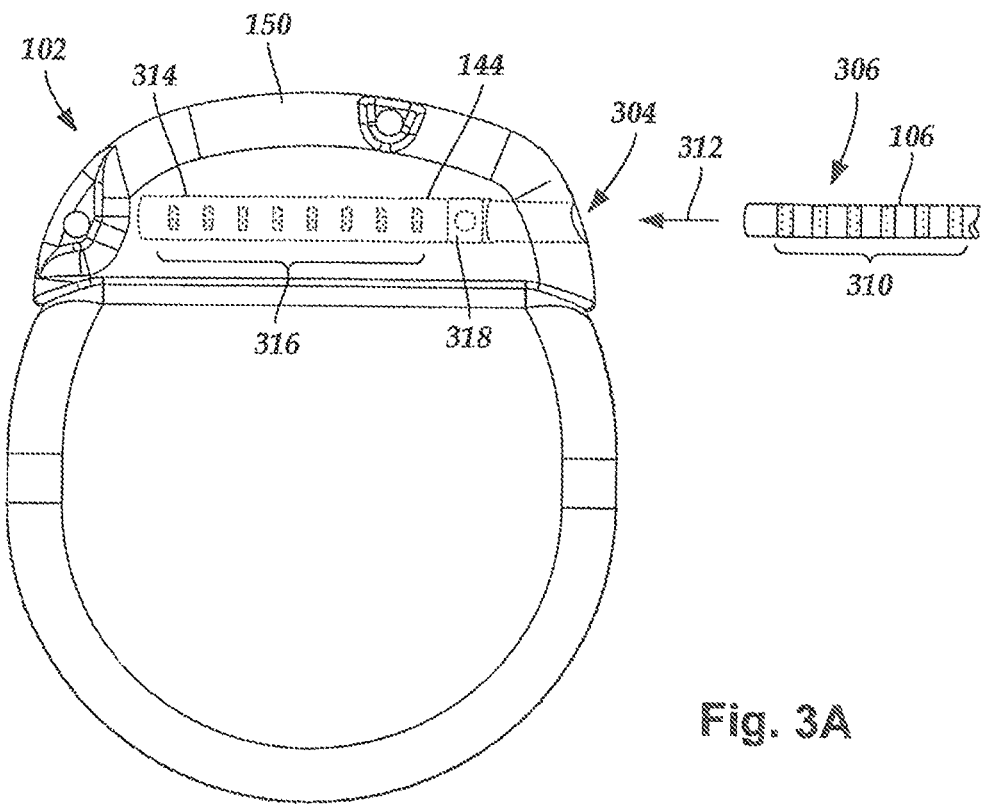
FIG. 3A is a schematic view of one embodiment of a connector assembly disposed in the control module of FIG. 1, the connector assembly configured and arranged to receive the proximal portion of one of the lead bodies of FIG. 1, according to the invention.
Figure 3B:
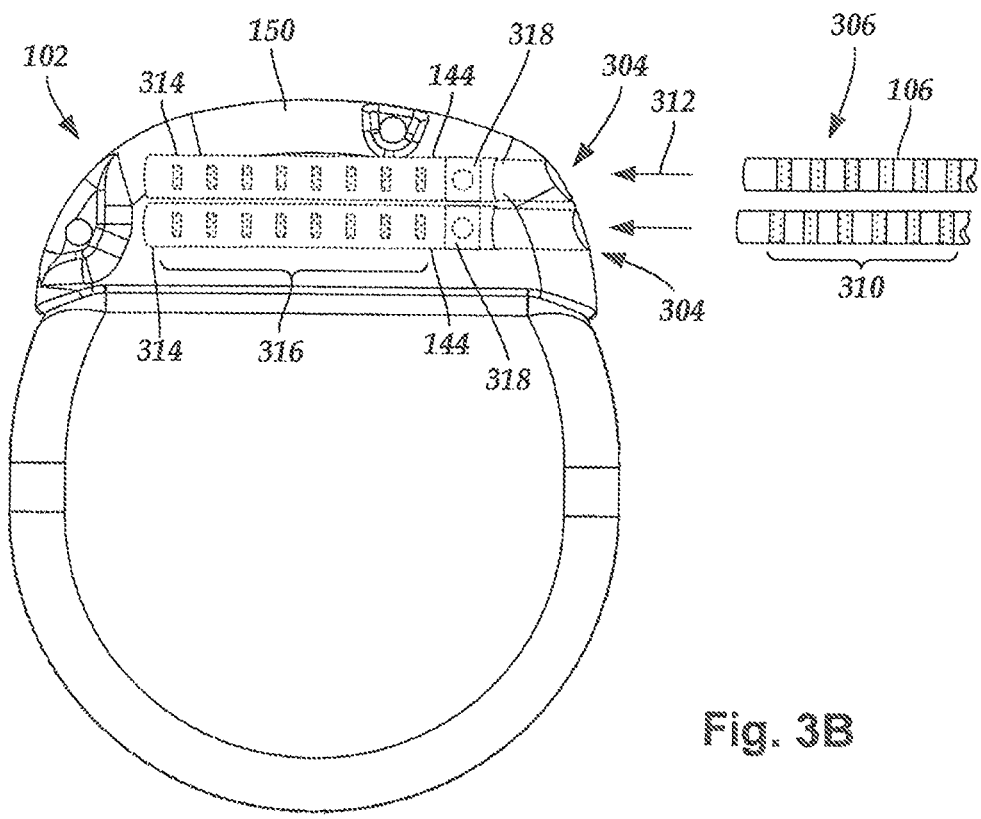
FIG. 3B is a schematic view of one embodiment of a plurality of connector assemblies disposed in the control module of FIG. 1, the connector assemblies configured and arranged to receive the proximal portions of the lead bodies of FIG. 1, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144.

In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
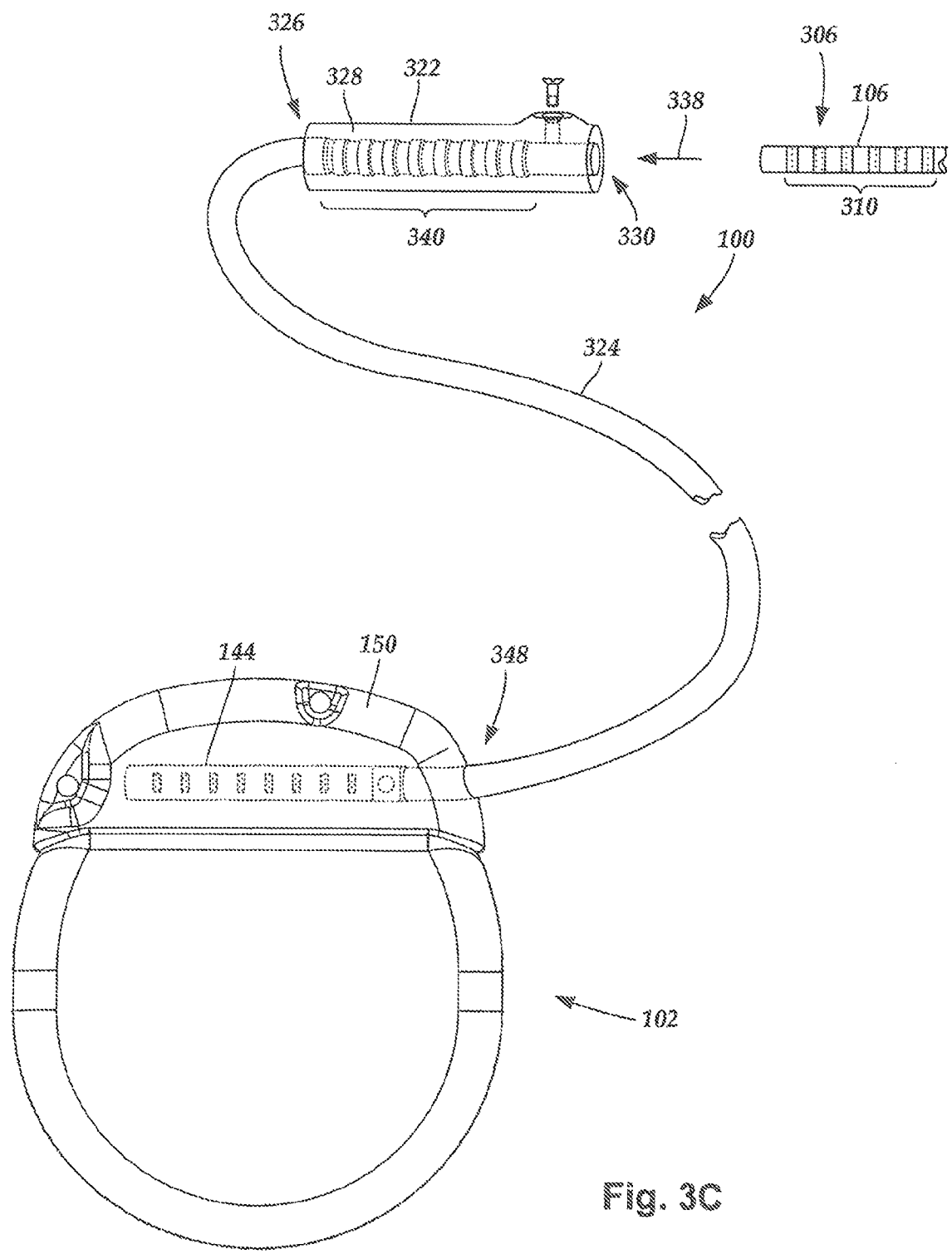
FIG. 3C is a schematic view of one embodiment of a proximal portion of one of the lead bodies of FIG. 1, a lead extension, and the control module of FIG. 1, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Conventional electrical stimulation systems may be potentially unsafe for use with magnetic resonance imaging ("MRI") due to the effects of electromagnetic fields in an MRI environment. A common mechanism for causing the electrical interactions between the electrical stimulation system and RF irradiation is common-mode coupling of the applied electromagnetic fields that act as a series of distributed sources along elongated conductive structures, such as leads, or conductors within leads. Common-mode induced RF currents can reach amplitudes of greater than one ampere in MRI environments. Such currents can cause heating and potentially disruptive voltages within electronic circuits.

Some of the effects of RF irradiation may include, for example, inducing current in the lead, causing undesired heating of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

One technique for reducing common-mode coupling is to arrange the one or more conductors into a configuration that diminishes the ability for applied electromagnetic fields to couple to the conductors, or that reduces the ability of the applied electromagnetic fields to create enough heat to damage patient tissue, or both. For example, one or more of the conductors connecting at least one terminal to an electrode (or to a conductive contact) can be arranged in a conductor path to eliminate or reduce the effect of RF irradiation, such as that generated during magnetic resonance imaging ("MRI"). The conductor path includes multiple units arranged in series. In some embodiments, the units are disposed along a single continuous conductor. In other embodiments, the units are separate conductive elements electrically coupled together.

Each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-layer region flanking at least one end of the multi-layer region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight.

In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
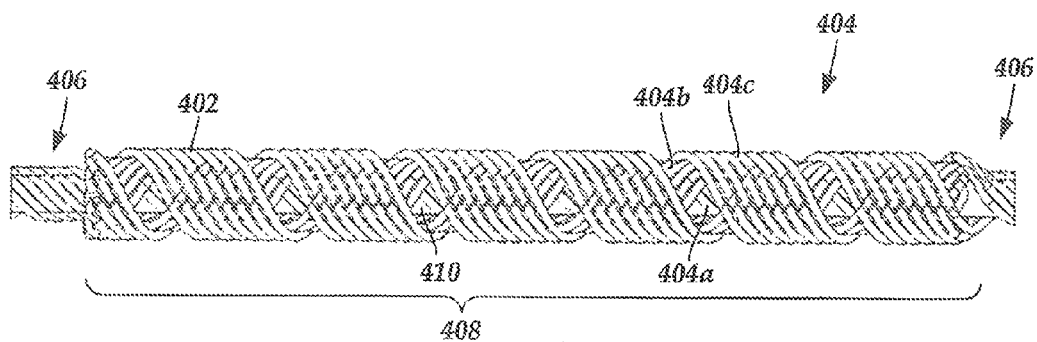
FIG. 4 is a schematic side view of one embodiment of portions of multiple conductors disposed along a conductor placement sleeve, the conductors arranged into coiled configurations, according to the invention.

FIG. 4 schematically illustrates one embodiment of a plurality of conductors 402. The conductors 402 are configured into multiple units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-layer regions, such as the single-layer regions 406, separated from one another by a multi-layer region, such as the multi-layer region 408.

In at least some embodiments, the conductors 402 are disposed along a conductor placement sleeve 410. The conductor placement sleeve 410 can be formed from any suitable biocompatible material including, for example, one or more polymers. In at least some embodiments, conductor insulation is disposed over the conductors 402 to encapsulate the conductors 402 and electrically isolate the conductors 402 from one another.

In at least some embodiments, one or more conductors having one or more units may be disposed in an elongated member (e.g., a lead or lead extension). In at least some embodiments, the ends of the conductors 402 can be coupled to terminals, electrodes, or conductive contacts. In preferred embodiments, each of the conductors in an elongated member is configured into units. In at least some embodiments, only a subset of the conductors disposed in an elongated member includes one or more units, the remaining conductors having a different arrangement (for example, a single conductor segment between the terminal(s) and electrode(s)/conductive contact(s)).

When one or more conductors are disposed along a lead body (or lead extension body), the arrangement of the conductor(s) may cause one or more open spaces to be formed along a longitudinal length of the lead body. For example, in the case of conductors arranged into coiled configurations (e.g., one or more of the above-described units, or the like), the lead may include one or more open spaces formed between two or more conductors, between two or more units of the same conductor (e.g., single layer regions 406), between two or more conductor segments of the same unit (e.g., between layers of coils), or between one or more portions of the same conductor segment (e.g., between individual coils).

When the lead is implanted in a patient, one or more of the electromagnetic properties of the lead (e.g., the conductivity, permittivity, inductance, capacitance, or the like) may change over time. As described below, these changes over time to the electromagnetic properties of the lead may be due, at least in part, to the presence of open spaces within the lead.

In many instances, implanted leads are disposed in fluid-containing portions of the patient. Such fluid-containing portions of the patient may potentially include any patient tissue. Conventional leads may include a body that is covered by an outer member (e.g., a jacket) that substantially prevents fluids (e.g., bodily fluids, introduced fluids, fluid vapor, or the like) in the local external environment from entering the lead. Over time, however, at least some fluid often seeps into the lead and at least partially fills the open spaces. As the fluid displaces air in the open spaces, one or more electromagnetic properties (e.g., permittivity, conductivity, or the like) within portions of the lead may begin to change over time such that portions of the lead with air in the open spaces have different electromagnetic properties from portions of the lead with fluid from the local external environment at least partially filling the open spaces.

Such changes to the electromagnetic properties within different portions of the lead can potentially cause a change in performance of the lead. For example, changes to the electromagnetic properties of the lead may amplify the ability for applied electromagnetic fields to couple to the conductors during exposure to certain RF energy (e.g., during performance of an MRI procedure), or increase the ability of the applied electromagnetic fields to create enough heat to damage patient tissue, or both, thereby reducing the performance of the lead during these conditions. In some cases, changes in performance may also include a diminished efficacy of stimulation (e.g., overstimulation, understimulation, unpredictable or uncontrollable stimulation, or the like or combinations thereof), or even a complete loss of efficacy of stimulation.

Despite much effort put forth by lead designers to create water-tight jackets, during lead operation at least some fluid from a local implantation environment will often eventually seep into the lead via, for example, manufacturing defects, broken seams or joints, broken down lead materials, or the like. Unfortunately, since such seepage is typically not planned for, the actual rate and extent of seepage of the fluid into the lead is not known at the time of implantation and may not be controllable.

One way to facilitate consistent performance of the lead, once implanted, is to design the lead to allow bodily fluids to enter the lead. In which case, the lead can be designed to modulate fluid ingress (e.g., seepage) into the lead. Moreover, the lead can be designed to operate while saturated with bodily fluids and withstand potential problems related to exposure to bodily fluids within the lead, such as corrosion or deterioration of components within the lead body.

As herein described, a lead can be designed to facilitate fluid ingress into the lead in a controlled manner instead of attempting to prevent, or delay, fluid ingress into the lead. Facilitating fluid ingress into the lead may include modulating at least one of the rate of fluid ingress into the lead or the extent of fluid ingress into the lead. In at least some embodiments, the lead includes a lead jacket that defines one or more apertures (e.g., pores, perforations, fenestrations, holes, slits, slots, gaps, punctures, clefts, cracks, fissures, orifices, or the like) that extend completely through the jacket to an interior portion of the lead and that, when the lead is implanted, enable bodily fluids (e.g., blood, cerebrospinal fluid, mucous, bile, chyle, lymph fluid, gastric juice, pleural fluid, peritoneal fluid, cerumen, or the like or combinations thereof) from a local environment exterior to the lead jacket to pass through the jacket and into the lead body.

Once fluid from the local environment within which the lead is implanted enters the lead, the local fluid displaces air-filled open spaces within the lead. Displacement of air from the open spaces in the lead reduces differences in one or more electromagnetic properties (e.g., permittivity, conductivity, or the like) between the open spaces in the lead and the local environment external to the lead. In at least some embodiments, as the differences in electromagnetic properties between the lead and the local environment are reduced the performance of the lead during exposure to RF irradiation (e.g., during an MRI procedure) improves as the lead performance becomes more consistent and predictable. Accordingly, it may be advantageous for the implanted lead to be filled with local fluid prior to the patient undergoing an MRI procedure to improve lead performance during the MRI procedure.

In at least some embodiments, lead performance includes electrical stimulation of patient tissue using the lead. It will be understood that patient tissue is stimulated via one or more electrodes (see e.g., 134 in FIGS. 1 and 2) disposed along the lead. In preferred embodiments, the local fluid that enters the lead jacket and displaces air-filled open spaces within the lead is not intended to directly contact conductors disposed within the lead jacket and is not intended form accessory conduction pathways along the lead.

Figure 5A:
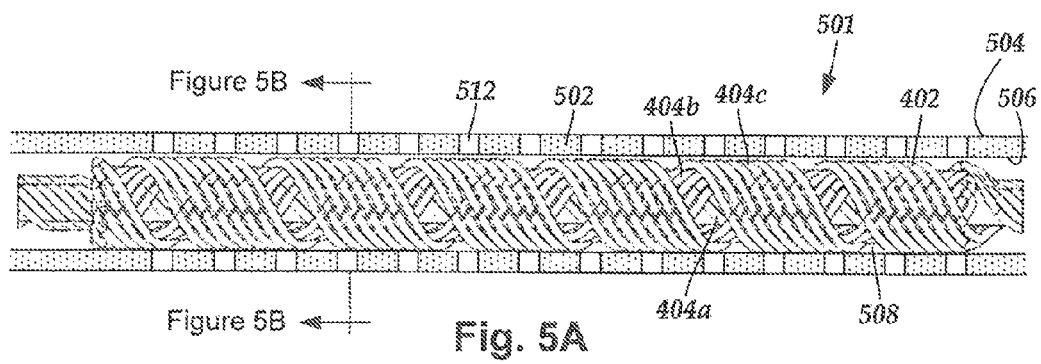
FIG. 5A is a schematic longitudinal cross-sectional view of one embodiment of a portion of a jacket disposed over a side view of the conductor portions of FIG. 4, the jacket defining apertures extending completely through the jacket, according to the invention.
Figure 5B:
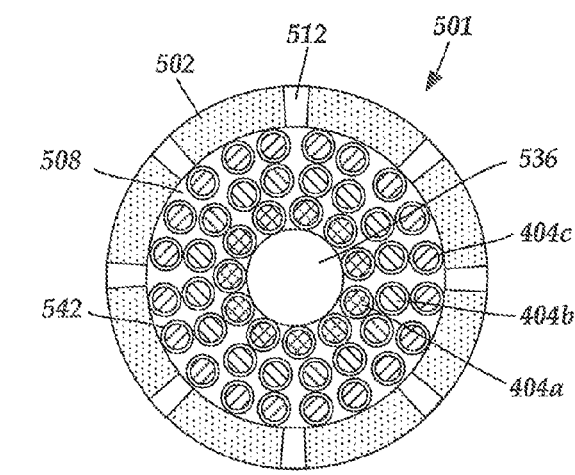
FIG. 5B is a schematic transverse cross-sectional view of one embodiment of the jacket portion of FIG. 5A disposed over the conductor portions of FIG. 4, the jacket defining apertures extending completely through the jacket, according to the invention.

FIG. 5A is a schematic view of one embodiment of an intermediate section of a lead 501. FIG. 5B is a schematic transverse cross-sectional view of one embodiment of the lead 501 along the section of the lead 501 shown in FIG. 5A. The lead 501 shown in FIGS. 5A-5B includes a jacket 502 (shown in FIG. 5A in longitudinal cross-section) disposed over the conductor portions 402 (shown in FIG. 5A in side view). In at least some embodiments, the jacket 502 extends the entire longitudinal length of the lead 501. In at least some embodiments, the jacket 502 extends less than the entire length of the lead 501. In at least some embodiments, the jacket 502 extends from the proximal-most electrode of the plurality of electrodes (see e.g., 134 in FIG. 2) to the distal-most terminal of the plurality of terminals (see e.g., 310 in FIGS. 3A-3B).

In FIGS. 5A-5B, the portions of the conductors 402 shown are disposed in one embodiment of a coiled configuration where the conductors 402 are configured into a plurality of units disposed over a stylet lumen 536. Each unit includes a first conductor segment 404*a*, a second conductor segment 404*b*, and a third conductor segment 404*c*. The conductor segments 404*a-c* are coiled into overlapping layers. In at least some embodiments, conductor insulation 542 is disposed over the conductors 402 to electrically isolate each of the conductors 402 from one another. As shown in FIGS. 5A-5B, the conductors 402 are arranged such that one or more open spaces, such as open space 508, are formed along a length of the lead 501. It will be understood that the conductors 402 can be arranged in any suitable configuration along the lead including, for example, configured into one or more of the above-described units, coiled, partially-coiled, straight, partially-straight, overlapped, non-overlapped, partially-overlapped, jumbled, tangled, or the like or combinations thereof.

The jacket 502 has an outer surface 504 and an inner surface 506. In at least some embodiments, the outer surface 504 of the jacket 502 forms an outer surface of the lead 501. Optionally, one or more layers of coatings, or annealing materials, or both, may be disposed over at least a portion of the outer surface 504 of the jacket 502. In at least some embodiments, the inner surface 506 of the jacket 502 is open to the conductors 402. The jacket 502 can have any suitable thickness. It will be understood that the thickness of the jacket 502 shown in FIGS. 5A-5B is meant to illustrate one embodiment and is dimensioned primarily for clarity of illustration. The thickness of the jacket 502 in relation to a diameter of the lead 501 can be either larger or smaller from what is shown in FIGS. 5A-5B.

Apertures, such as aperture 512, are defined along the jacket 502. In at least some embodiments, the apertures 512 are defined along the entire jacket 502. In other embodiments, the apertures 512 are defined solely along one or more discrete regions of the lead. The apertures 512 each extend through the jacket 502 from the outer surface 504 of the jacket 502 to the inner surface 506 of the jacket 502 such that the conductor insulation 542 surrounding the conductors 402 is exposed to the local environment external to the lead 501. It will be understood that the diameters of the apertures 512 shown in FIGS. 5A-5B (as well as in other figures) are meant to illustrate one embodiment and are dimensioned primarily for clarity of illustration. As described in more detail below, the sizes and shapes of the apertures 512 can vary widely from what is shown in FIGS. 5A-5B. In at least some embodiments, the apertures 512 are sized such that the apertures 512 are large enough to facilitate fluid ingress into the lead 501, yet small enough to enable the jacket 502 to provide gross coverage of the internal lead components and mechanical stability to the underlying portions of the lead.

In at least some embodiments, the jacket 502 is formed as a single lumen extrusion. In at least some embodiments, the jacket 502 is braided or weaved. In at least some embodiments, the jacket 502 is etched, ablated, molded, or perforated to form the apertures 512. In some embodiments, the jacket is pre-formed with apertures prior to distribution to the implanting practitioner (i.e., the apertures are pre-defined). In other embodiments, the jacket 502 is modified after distribution to the implanting practitioner. In at least some embodiments, the jacket 502 is modified prior to being disposed over the lead body. In at least some other embodiments, the jacket 502 is modified after the jacket 502 is disposed over the lead body.

The jacket 502 can be formed from any biocompatible, biostable material suitable for implantation. In at least some embodiments, such as when the jacket 502 is modified after distribution to the implanting practitioner, the jacket 502 is formed from, for example, one or more polymers, hydrogels, expanded polymers, porous coatings, or the like or combinations thereof.

Turning to FIGS. 6A-8, the apertures 512 can be formed in many different shapes, sizes, and orientations. Moreover, the apertures can be defined along the jacket in any number and in any suitable pattern. It will be understood that the apertures shown in FIGS. 6A-8 are simply meant to be examples. The apertures may be either larger or smaller in size in relation to the jacket from what is shown in FIGS. 6A-8.

Different sizes, shapes, and orientations of the apertures may affect the rate of fluid ingress. For example, different fluid properties (e.g., viscosity, or the like) of a particular fluid may affect whether or not that fluid passes through a given aperture. Additionally, different orientation or patterning of the apertures may affect the location of fluid ingress into the lead. For example, positioning (or orienting) apertures over a portion of the lead that includes open spaces within the lead versus positioning apertures over a portion of the lead without open spaces within the lead may affect whether or not a fluid passes through a given aperture.

Thus, it may be advantageous to use apertures with different shapes, different sizes, or arranged into specific patterns in order to modulate the rate or the extent (or both) of fluid ingress upon implantation. It may also be advantageous to arrange the apertures 512 along at least a portion of the lead 501 such that the size, shape, orientation, and arrangement of the apertures are configured and arranged to promote tissue ingrowth to facilitate anchoring of the lead 501 to patient tissue.

In at least some embodiments, the apertures are distributed along the jacket 502 such that the timing, or the completeness, or both, of air displacement within the lead 501 by local fluids can be modulated. In at least some embodiments, the apertures 512 are distributed along the jacket 502 such that at least 50% of the air disposed in open spaces within the lead 501 is displaced by fluid from the local environment within ten days, nine days, eight days, seven days, six days, five days, four days, three days, two days, one day, eighteen hours, twelve hours, six hours, four hours, three hours, two hours, or one hour, or less.

In at least some embodiments, the lead 501 is pre-soaked in a liquid prior to implantation. In which case, the pre-soaking may fill at least some of the open spaces within the lead 501 prior to implantation. In at least some embodiments, the lead 501 is pre-soaked in fluid from the target implantation location. In at least some other embodiments, the lead 501 is pre-soaked in one or more other fluids, such as water, saline solution, or the like. In at least some embodiments, filling at least some of the open spaces within the lead 501 with fluid other than fluid from the target implantation location may provide similar, or even identical, lead performance as would be achieved using fluid from the target stimulation location.

In at least some embodiments, the apertures are designed to modulate the extent of fluid ingress into the lead. In which case, fluid-ingress equilibrium may be reached after a particular amount of time. When fluid-ingress equilibrium is reached, the lead tends to not receive any additional fluid from the local external environment. In at least some embodiments, when fluid-equilibrium is reached at least one of the permittivity or the conductivity of the open spaces within the lead are equal to the at least one of the permittivity or the conductivity of the fluid from the local environment external to the lead. The percentage of the open space within the lead that is filled by fluid from the local external environment when the lead is at the fluid-ingress equilibrium may vary, depending on many different factors including, for example, the shape, size, orientation, and arrangement of the apertures, the configuration of the conductors within the lead, one or more properties of the local fluid (e.g., viscosity, charge, or the like or combinations thereof), or the like or combinations thereof. The percentage of open space within the lead that is filled by fluid from the local external environment when the lead is at the fluid-ingress equilibrium may be, for example, at least 50%, 55%, 60%, 65%, 70%, 75%, 80%, 85%, 90%, 95%, 96%, 97%, 98%, or 99%, or more of the open space within the lead. It will be understood that the above percentages of open spaces within the lead do not include open space within the stylet lumen (see e.g., 536 in FIG. 5B) which may be sealed from fluid ingress.

Figure 6A:
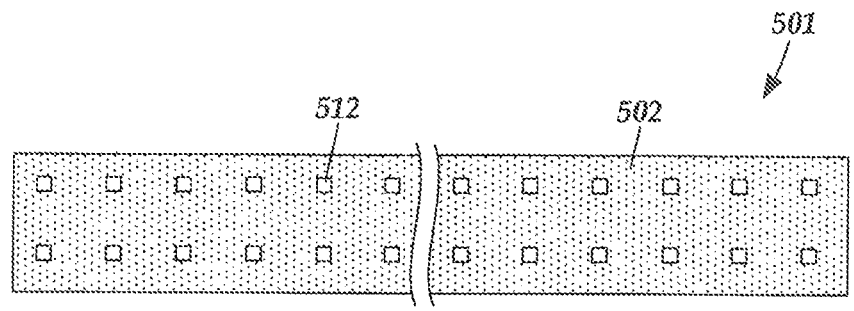
FIG. 6A is a schematic side view of one embodiment of apertures defined along the jacket of FIG. 5A, according to the invention.
Figure 6B:
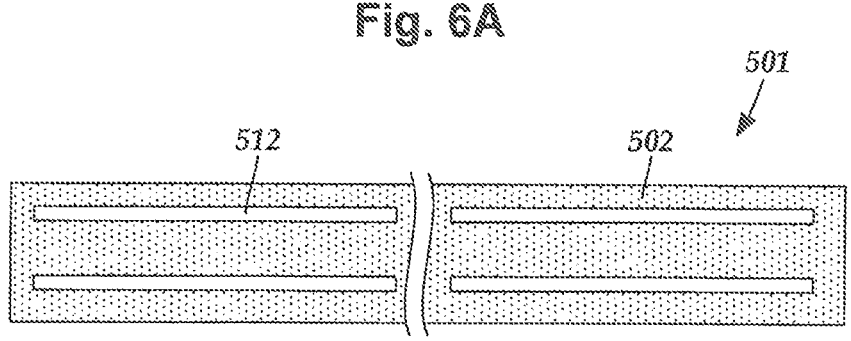
FIG. 6B is a schematic side view of another embodiment of apertures defined along the jacket of FIG. 5A, according to the invention.

Turning to FIGS. 6A-6B, in at least some embodiments the apertures are evenly distributed along the jacket. FIG. 6A is a schematic side view of one embodiment of apertures 512 equally distributed along the jacket 502. FIG. 6B is a schematic side view of another embodiment of apertures 512 defined along the jacket 502. In each of FIG. 6A and FIG. 6B, the apertures 512 are shown as each being of equal size. In FIG. 6A, the apertures 512 are shown as each having the same round shape. In FIG. 6B, the apertures 512 are shown as each having the same elongated rectangular shape.

In alternate embodiments (see e.g., FIGS. 6C-6D), the jacket 502 includes apertures 512 having at least two different shapes (e.g., round, oval, triangular, rectangular, star-shaped, cruciform-shaped, or the like). It will be understood that the apertures 512 can, alternately or additionally, be formed into one or more non-geometric shapes.

In FIGS. 6A-6B, the apertures 512 are shown arranged into a regular, repeating pattern. In particular, FIGS. 6A-6B show the apertures arranged into columns that are defined along a length of the lead, and rows that are defined around a circumference of the jacket 502. In at least some alternate embodiments, the apertures 512 are arranged into an irregular, repeating (or non-repeating) pattern (see e.g., FIG. 6D). In at least some alternate embodiments, the apertures 512 are arranged into a regular, repeating pattern that does not include at least one of rows or columns.

Figure 6C:
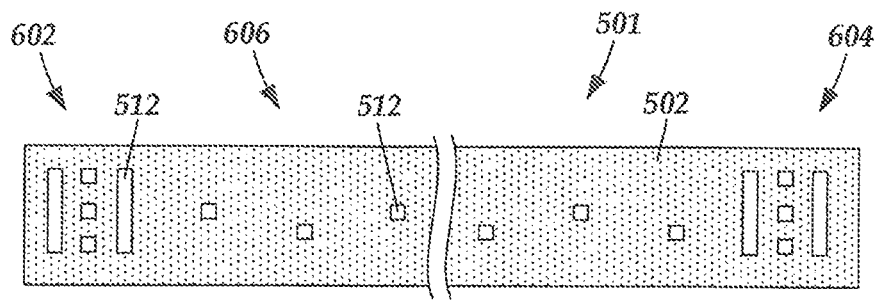
FIG. 6C is a schematic side view of yet another embodiment of apertures defined along the jacket of FIG. 5A, according to the invention.
Figure 6D:
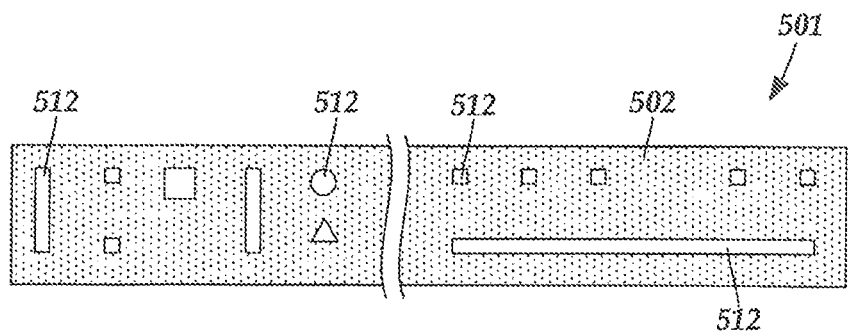
FIG. 6D is a schematic side view of another embodiment of apertures defined along the jacket of FIG. 5A, according to the invention.

Turning to FIGS. 6C-6D, in at least some embodiments the apertures are unevenly distributed along the jacket. FIG. 6C is a schematic side view of one embodiment of the jacket 502 that includes apertures 512 unevenly distributed along a length of the jacket 502. In FIG. 6C, the apertures 512 are also shown as having several different shapes.

In FIG. 6C, a higher density of apertures 512 is shown along the opposing ends 602, 604 of the jacket 502 than in an intermediate region 606 of the lead 501. It may be advantageous to provide a higher density of apertures 512 along one or more of the opposing ends 602, 604 of the jacket 502 than in an intermediate region 606 of the lead 501 to promote a faster rate of fluid ingress at one or more of the ends 602, 604 of the lead 501, in proximity to the electrodes or terminals, than in other portions of the lead 501.

In some embodiments, a higher density of apertures 512 is defined along only one of the two opposing ends 602, 604. In alternate embodiments, a higher density of apertures 512 is disposed along at least a portion of the intermediate region 606 than one or more of the opposing ends 602, 604. In at least some embodiments, the apertures 512 are distributed along the length of the lead 501 such that the aperture density is higher in proximity to the plurality of electrodes (see e.g., 134 in FIGS. 1-2) than along the intermediate region 606 of the lead 501. In at least some embodiments, the apertures 512 are distributed along the length of the lead 501 such that the aperture density is higher in proximity to the plurality of terminals (see e.g., 310 in FIGS. 3A-3B) than along the intermediate region 606 of the lead 501.

FIG. 6D is a schematic side view of another embodiment of the jacket 502 that includes apertures 512 unevenly distributed along a length of the jacket 502. In FIG. 6D, multiple apertures 512 are shown distributed along the length of the jacket 502 in a non-repeating, irregular pattern. The apertures 512 shown in FIG. 6D also have several different sizes and shapes.

Figure 7A:
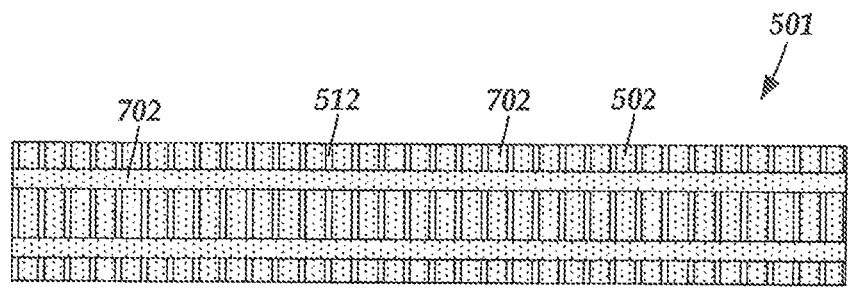
FIG. 7A is a schematic side view of one embodiment of apertures defined between portions of the jacket of FIG. 5A, according to the invention.
Figure 7B:
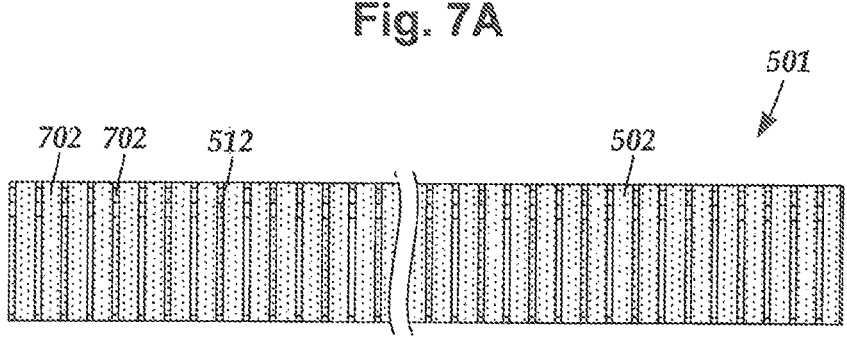
FIG. 7B is a schematic side view of another embodiment of apertures defined between portions of the jacket of FIG. 5A, according to the invention.
Figure 7C:
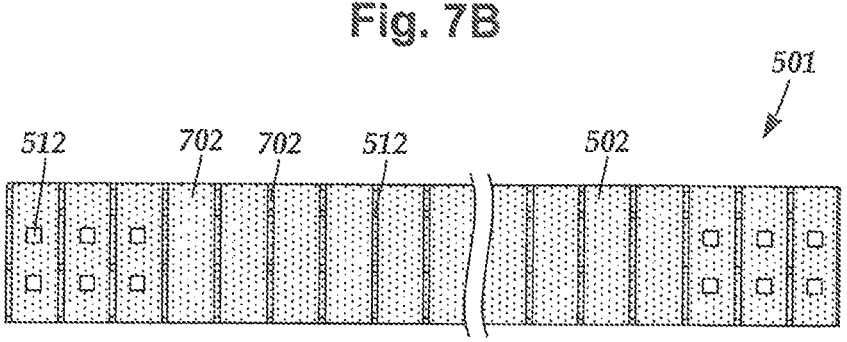
FIG. 7C is a schematic side view of one embodiment of apertures defined along portions of the jacket of FIG. 5A, as well as apertures defined between portions of the jacket, according to the invention.

Turning to FIGS. 7A-7C, in at least some embodiments the jacket is formed from strips (e.g., fibers, strands, or the like) of material that are braided or woven together. In which case, the apertures can be formed in the material itself, between adjacent strips of the material, or both.

FIG. 7A is a schematic side view of one embodiment of the jacket 502 formed from braided, or woven, material. FIG. 7B is a schematic side view of another embodiment of the jacket 502 formed from braided, or woven, material. FIG. 7C is a schematic side view of yet another embodiment of the jacket 502 formed from braided, or woven, material. In each of FIGS. 7A-7C, the apertures 512 are shown defined between strips, such as exemplary strip 702, of material that are interleaved, intertwined, or overlapped, with one another to form the braided, or woven, jacket 502. The strips 702 can be formed in any suitable dimensions (e.g., thickness, width, length, or the like), in any suitable count, and in any suitable number of layers of strips 702. In FIG. 7C, the apertures 512 are also shown defined in the braided, or woven, material itself.

Figure 8:
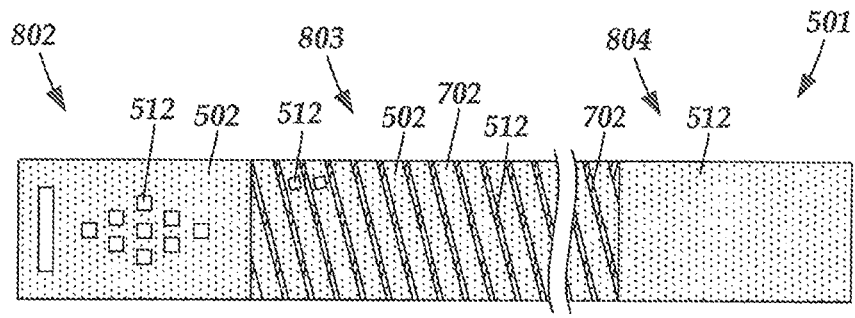
FIG. 8 is a schematic side view of one embodiment of the jacket of FIG. 5A that includes a first region with apertures defined along portions of the jacket, a second region with apertures defined between portions of the jacket, and a third region that does not include apertures, according to the invention.

Turning to FIG. 8, in at least some embodiments, the jacket includes one or more regions without apertures. FIG. 8 is a schematic side view of one embodiment of the jacket 502 having multiple jacket regions 802-804. The first region 802 includes apertures 512 defined along portions of the jacket 502. The second region 803 includes apertures 512 defined between strips 702 of the jacket 502. The third region 804 of the jacket 502 does not include any apertures 512. In at least some embodiments, at least two of the different regions 802-804 have different aperture densities from one another. In at least some embodiments, each of the different regions 802-804 has a different aperture density than each of the other regions 802-804. It will be understood that the lead 501 may include different combinations of two or more of the jacket regions 802-804 in any suitable configuration along the length of the lead 501.

It may be advantageous to include multiple different regions along the length of the lead 501. In at least some embodiments, the apertures 512 are distributed along the length of the lead 501 such that the aperture density is adjusted based on which body tissues a particular portion of the lead 501 is expected to abut when implanted in the patient. For example, in at least some embodiments the lead 501 is implanted into the patient's epidural space. In which case, a different aperture density may be desired along portions of the lead 501 expected to be disposed in the epidural space after implantation, as compared to portions of the lead 501 expected to be disposed in the tunneling path, or control-module pocket.

The jacket 502 can include any suitable aperture density along any suitable portion of the length of the lead 501. In at least some embodiments, the jacket 502 has an aperture density of at least one, two, three, four, five, six, seven, eight, nine, ten, or more aperture(s) per square centimeter. In at least some embodiments, the jacket 502 has an aperture density of no less than twenty, fifteen, ten, or less apertures per square centimeter. As discussed above, in some embodiments the apertures 512 are evenly distributed along the length of the lead 501 while, in other embodiments, the apertures 512 are unevenly distributed along the length of the lead 501.

It will be understood that the jacket 502 can be used in conjunction with leads designed for many different uses including, for example, spinal cord stimulation, deep brain stimulation, cardiac pacing, cardiac defibrillation, or the like. Additionally, the jacket 502 can be used in conjunction with many different types of leads including, for example, percutaneous leads, paddle leads, lead extensions, or the like.

Figure 9:
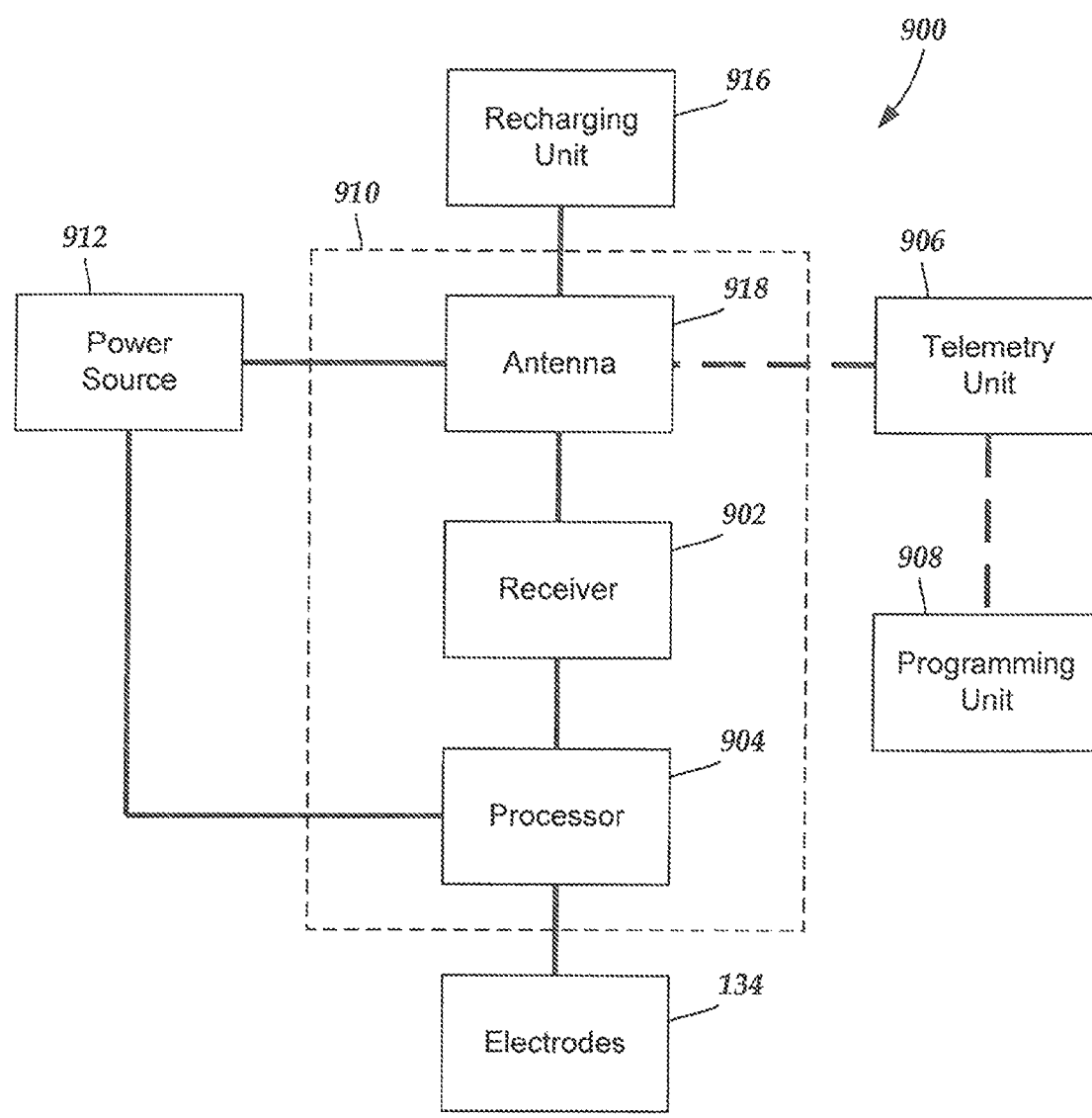
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead for stimulating patient tissue, the lead comprising:
   a lead body having a distal end, a proximal end, and a longitudinal length;
   a jacket disposed over at least a portion of the longitudinal length of the lead body, the jacket having an outer surface and an opposing inner surface, at least a portion of the outer surface of the jacket forming at least a portion of an outer surface of the lead, at least a portion of the inner surface of the jacket open to the lead body, the jacket defining a plurality of apertures along the outer surface of the jacket with each of the plurality of apertures extending completely through the jacket to the inner surface;
   a plurality of electrodes disposed along the distal end of the lead body;

a plurality of terminals disposed along the proximal end of the lead body;

a plurality of conductors electrically coupling the plurality of electrodes to at least one of the terminals; and conductor insulation disposed over each of the plurality of conductors;

wherein at least a portion of the conductor insulation is in fluid communication with the local environment external to the lead via the plurality of apertures, wherein the apertures are spaced-apart and separate from the electrodes and terminals.

2. The lead of claim 1, wherein the plurality of apertures are evenly distributed along the longitudinal length of the lead body.

3. The lead of claim 1, wherein the plurality of apertures are distributed along the jacket with a higher concentration of apertures along the distal end of the lead body than along an intermediate region of the lead body.

4. The lead of claim 1, wherein the plurality of apertures are defined along the jacket with a higher concentration of apertures along the proximal end of the lead body than along an intermediate region of the lead body.

5. The lead of claim 1, wherein the plurality of apertures are each of equal size.

6. The lead of claim 1, wherein the plurality of apertures are each of equal shape.

7. The lead of claim 1, wherein the jacket is formed from at least one of a braided or woven material.

8. The lead of claim 1, wherein the jacket is disposed over the entire longitudinal length of the lead body proximal to a proximal-most electrode of the plurality of electrodes and distal to a distal-most terminal of the plurality of terminals.

9. The lead of claim 1, wherein at least one of the plurality of conductors is arranged into a coiled configuration.

10. The lead of claim 1, wherein at least one of the plurality of conductors is arranged into a plurality of units.

11. An electrical stimulating system comprising:

the lead of claim 1;

a control module configured and arranged to electrically couple to the lead body, the control module comprising a housing, and an electronic subassembly disposed in the housing; and at least one connector configured and arranged for receiving the lead body, the at least one connector having a first end and an opposing second end, the at least one connector comprising a connector housing defining a port at the first end of the connector, the port configured and arranged for receiving the proximal end of the lead body, and a plurality of connector contacts disposed in the connector housing, the plurality of connector contacts configured and arranged to couple to the plurality of terminals of the lead body when the lead body is inserted into the port of the connector housing.

12. A method for stimulating patient tissue with an implantable lead, the method comprising:

advancing the lead of claim 1 to a fluid-containing target stimulation location within a patient;

coupling the lead to a control module, the control module comprising a pulse generator;

generating stimulation energy from the pulse generator for stimulating patient tissue via the plurality of electrodes of the lead; and stimulating patient tissue, via at least one of the plurality of electrodes of the lead, using the generated stimulation energy after sufficient fluid from the fluid-containing target stimulation location has passed through the plurality of apertures defined in the jacket of the lead and filled at least some open spaces within the lead to reduce at least one of the permittivity or the conductivity of the open spaces within the lead to a same level as the fluid from the fluid-containing target stimulation location that is external to the lead.

13. The method of claim 12, wherein stimulating patient tissue after enough fluid from the fluid-containing target stimulation location has passed through the plurality of apertures comprises using fluid from the target stimulation location.

14. The method of claim 12, wherein stimulating patient tissue after enough fluid from the fluid-containing target stimulation location has passed through the plurality of apertures comprises submerging at least a portion of the lead in a liquid prior to advancing the lead to the fluid-containing target stimulation location.

\* \* \* \* \*